(12) United States Patent
Barlow et al.

(10) Patent No.: US 6,168,824 B1
(45) Date of Patent: Jan. 2, 2001

(54) PAINT VISCOSITY MEASURING SYSTEM

(75) Inventors: Timothy A. Barlow, Clinton Township; Wayne T. Rozan, Chesterfield, both of MI (US)

(73) Assignee: DaimlerChrysler Corporation, Auburn Hills, MI (US)

( * ) Notice: Under 35 U.S.C. 154(b), the term of this patent shall be extended for 0 days.

(21) Appl. No.: 09/444,593

(22) Filed: Nov. 22, 1999

(51) Int. Cl.⁷ ............................................ B05D 1/02
(52) U.S. Cl. .................. 427/8; 427/345; 427/421; 137/4; 137/7; 137/92; 239/75; 239/101
(58) Field of Search ................ 137/4, 7, 92; 239/75, 239/101; 427/8, 345, 421

(56) References Cited

U.S. PATENT DOCUMENTS

| | | | |
|---|---|---|---|
| 2,762,652 | 9/1956 | Carter | 299/86 |
| 3,282,323 | 11/1966 | Katz et al. | 158/36 |
| 4,263,091 | 4/1981 | King | 159/44 |
| 4,278,205 | 7/1981 | Binoche | 239/75 |
| 4,592,305 | 6/1986 | Scharfenberger | 118/677 |
| 4,738,219 | 4/1988 | Fujisawa | 118/666 |
| 4,878,649 | 11/1989 | Baba et al. | 251/121 |
| 5,096,120 | 3/1992 | Luckarz | 239/75 |
| 5,330,783 | * 7/1994 | Saidman et al. | 427/8 |
| 5,433,587 | 7/1995 | Bankert et al. | 417/44.2 |

* cited by examiner

Primary Examiner—Katherine A. Bareford
(74) Attorney, Agent, or Firm—Lawrence J. Shurupoff

(57) ABSTRACT

A method of monitoring and regulating the viscosity of paint in an automotive paint application is provided. The method includes delivering paint to the paint application system with a pump. Continuously monitoring the pressure that the paint is delivered to the paint application by the pump. Returning the paint which is not applied to the automotive vehicle by the paint application system through a return line. Continuously monitoring the pressure of the paint flowing through the return line. Continuously calculating the viscosity from the pressure differential between the delivery pressure and the return line pressure and the flow rate in the return line and the fluid resistance of the paint application system to determine the viscosity of the paint. Delivering the paint from the return line to a sump. Selectively adding thinners to the paint to cause the paint to have a predetermined level of viscosity.

5 Claims, 1 Drawing Sheet

PAINT VISCOSITY MEASURING SYSTEM

FIELD OF THE INVENTION

The present invention relates to a method for regulating the viscosity of a liquid paint in an automotive vehicle paint application system. In particular, the present invention relates to a method wherein the viscosity of the liquid paint in an automotive vehicle paint application system is continuously monitored and may be continuously regulated on a real time basis.

BACKGROUND OF THE INVENTION

In automotive coating, the so-called clear coat technique (sometimes referred to as two-coat one-bake technique) is employed which comprises applying a metallic base paint composition, called a top coat, containing a metallic pigment, to a steel substrate or other material. The steel substrate or other material is provided in advance with undercoat and intermediate coat primers. Then, without curing of the resulting top coat paint film, a clear paint composition is applied over the top coat in a wet-on-wet manner. The top coat and clear paint are then cured simultaneously.

The prior art paints used in said two-coat one-bake technique are mostly organic solvent based. However, from the viewpoints of safety during coating, reduction of environmental pollution and preserving resources, among others, water-based paints have been earnestly desired in recent years. For this purpose, various water-based paints have been developed for automobile coating.

Various curing systems for water-based clear coating paints have been proposed. They include, curing systems containing a hydroxyl group (including a blocked hydroxyl group), a carboxyl group (including a blocked carboxyl group wherein the hydroxyl group of the carboxyl group is blocked), a phosphoric acid group (including a blocked phosphoric acid group wherein the hydroxyl group of the phosphoric acid group is blocked) or an acid anhydride group; curing systems containing such a group as described above and also a silyl group (including a hydrolyzable silyl group blocked with a hydrolyzable group) and/or an epoxy group; curing systems containing an acetoacetyl group and a vinyl ether group or a vinyl thio ether group (hereinafter referred to simply as a vinyl (thio) ether group); curing systems containing a vinyl (thio) ether group and a carboxyl group or a silyl group; curing systems containing an alicyclic epoxy group and a silyl group; and curing systems containing a silyl group or an alicyclic epoxy group singly. In such curing systems, a curing catalyst is usually used to accelerate the curing reaction of the functional groups.

In the clear coat technique, the clear coat paint and the base coat paint (top coat) are stored separately in storage vessels until immediately before the coating thereof of the automotive vehicle.

In most auto plant assembly paint systems a plurality of colors are available for instant use. Each color requires a separate base coat application system and conventionally, each application system includes a circulation network wherein a circulation pump causes the base paint to flow through the network conduits. The network includes a plurality of base paint distributors, such as spray guns or spray nozzles, which may be fixed, robotically operated or hand held, and one or more of the paint distributors may be in operation at a time. It is necessary to design the application system to be capable of handling sufficient paint if all the distributors are in operation simultaneously, but usually only a small percentage of the capacity of the application network is used at any one time.

The base paint application system is basically "closed" wherein the base paint circulates in a loop, and it is necessary to add base paint to the loop to replace that ejected from the nozzles. The circulation of the base paint in the application system is at a high rate and the base paint will be cycled many times if usage is low. Problems have been experienced with existing paint circulation systems with respect to paint particles settling within the network conduits, and degradation of the base paint occurs during extended circulation, including the degradation of metallic flakes and the like which may be added to the paint for aesthetic purposes. Additionally, existing paint application systems do not permit a ready indication of the viscosity of the base paint. As viscosity changes, the quality of the applied paint will change, and to provide optimum results, viscosity of the paint must be continuously known.

As mentioned previously, quality automotive paint finishing requires precise control of all parameters, paint viscosity being the highest priority. Prior to the present invention, to insure uniform paint viscosity, the paint application operator would measure and adjust the viscosity by adding various solvents as required. The viscosity was typically measured manually using either a Brookfield Viscometer or a #4 Ford Cup after taking a sample from the automotive vehicle paint application system's batch tank. Specialized instruments are available for measuring viscosity without utilizing a Brookfield Viscometer or #4 Ford Cup. However, such instruments are expensive and typically require frequent calibration. It is desirable to provide a method of continuously monitoring the viscosity of paint in an automotive vehicle body paint application system which does not require manual operation or the utilization of very expensive instrumentation requiring frequent calibration.

SUMMARY OF THE INVENTION

To meet the above-noted and other unfulfilled desires, the revelation of the present invention is brought forth. The present invention makes manifest a freedom of continuously monitoring the viscosity of liquid paint in an automotive vehicle paint application system without manual intervention. The present inventive viscosity monitoring method provides liberty from expensive instrumentation requiring frequent calibration. In a preferred embodiment the present invention additionally provides a method of regulating the viscosity of a liquid paint in an automotive vehicle paint application system. The method includes delivering paint to the paint application system with a pump. Continuously monitors the pressure that the paint is delivered to the paint application by the pump. Returning the paint which is not applied to the automotive vehicle by the paint application system through a return line. Continuously monitoring the pressure of the paint flowing through the return line. Continuously measuring the flow rate of the paint returning through the return line. Continuously calculating the viscosity from the pressure differential between the delivery pressure and the return line pressure and the flow rate in the return line and the fluid resistance of the paint application system to determine the viscosity of the paint. Delivering the paint from the return line to a sump. Adding thinners to the paint to cause the paint to have a predetermined regulated level of viscosity.

It is an object of the present invention to continuously monitor the viscosity of a liquid paint in an automotive vehicle paint application system.

It is an object of the present invention to provide a method of regulating the viscosity of a liquid paint in an automotive vehicle paint application system.

The above noted and other objects of the present invention will become apparent to those skilled in the art from a review of the invention as it is provided in the accompanying drawing and detailed description of the preferred embodiment.

DETAILED DESCRIPTION OF THE PREFERRED EMBODIMENT

Figure 1:
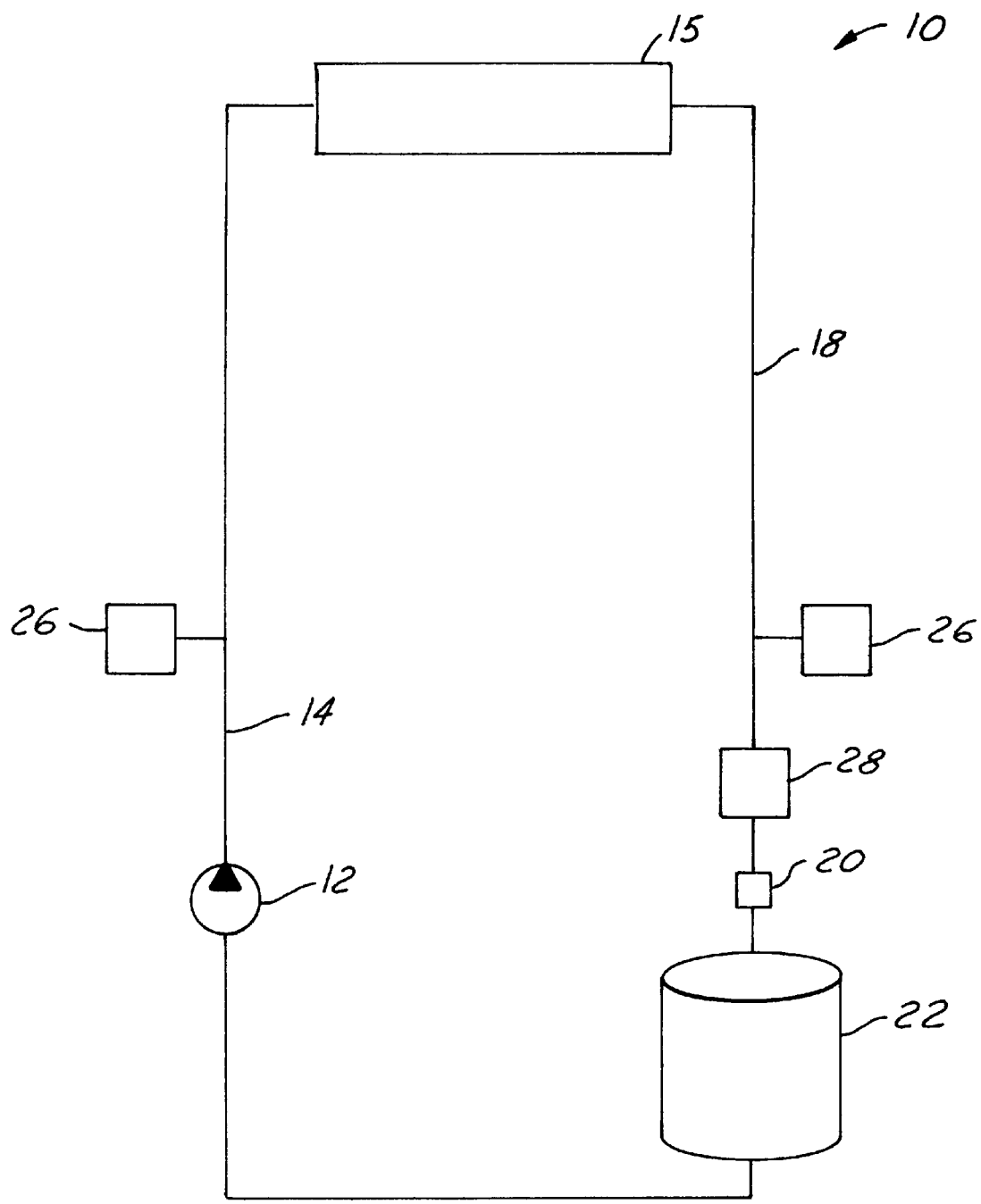
FIG. 1 is a schematic view of an automotive vehicle body paint application system which utilizes the method of the present invention wherein the viscosity of the paint is regulated.

FIG. 1 is a schematic view of a base coat vehicle body paint application system 10. The paint application system 10 is for the base coat which includes the color. A similar system exists in parallel for the clear coat. A typical base coat utilized is water-borne white sold by PPG, of Pittsburgh, Pa. The paint is delivered from a satellite paint facility by the paint manufacturer, pre-reduced to spray viscosity so that additional solvent is not required and charged to the volatile organic compound (VOC) usage of the assembly plant. The assembly plant must not exceed its permit limits for total annual VOCs emitted. If the viscosity of the paint increases due to evaporation, it is acceptable to use solvent to lower the viscosity. The paint is delivered to the paint application system by a pump 12. The pump 12 is a turbine pump manufactured by Graco, Inc. The pump will typically deliver paint to the system at 180–200 psi and at a 10–25 GPM volume flow rate. Flow rate is dependant upon size and design of the paint application system 10. The line 14 will typically be two inches in diameter and the paint typically travels at a minimum flow velocity of one ft. per second velocity. A pressure transducer such as a 350 model manufactured by Viatran of Grand Island, N.Y., continuously monitors the pressure of the paint which is delivered to the paint application system 10 by the pump 12. The temperature of the paint will typically be in a range of 70 to 90° F. The paint is delivered to the paint area 15 where a plurality of branch lines (not shown) connect with various stationary and robotic sprayers to spray the paint on the vehicles which pass by the sprayers on a conveyor line. Although all the sprayers can be utilized at once, typically 10% of the paint is sprayed by the sprayers and the remaining 90% is recirculated to the return line 18. The return line 18 typically will be a two inch diameter. The paint in the return line 18 is directed to a back pressure regulator 20 which is typically set to 100–80 psi pressure. Pressure regulator 20 dumps into a batch tank or sump 22. The back pressure regulator is a constant-pressure type pressure regulator. A typical type is a 223–824 model manufactured by Graco, Inc. of Minneapolis, Minn.

Prior to the back pressure regulator 20 there is provided a pressure transducer 26 for continuously monitoring the pressure in the return line 18. The pressure transducer 26 is a 350 type pressure transducer manufactured by Viatran of Grand Island, N.Y. Subsequent to the pressure transducer 26 is a flow meter 28. The flow meter 28 as shown is a gear-type flow meter. The flow meter is model FD-151 manufactured by Flow Data, of Richardson, Tex. The flow meter 28 continuously monitors the flow of paint in the return line 18.

In operation, paint is delivered to the automotive vehicle body paint application system 10 by the pump 12. The pressure transducer 14 continuously monitors the pressure (180 psi) of the paint delivered. Paint is then selectively delivered to a series of selectively open/shut nozzles 16 to various vehicles which pass by on the assembly line. Preferably, the paint delivered by the pump 12 is at 80° F. temperature and at a pressure in typical values. The excess paint which is not utilized by the sprayer 16 is delivered to the return line 18. The pressure transducer 26 continuously monitors the pressure of the line 18. The flow meter 28 continuously monitors the flow of fluid passing through the return line 18. A back pressure regulation valve 20 insures a pressure (100 psi) in the return line. The paint is then delivered to the batch tent 22 which serves as a sump for the pump 12. A pressure differential exists between the pressure transducer 14 and the pressure transducer 26. Viscosity is determined by the differential of pressure, divided by the product of mass (volumetric) flow rate times a constant representative of the fluid resistance of the paint application system. The formula for pressure drop through a system for laminar flow conditions (where the Reynolds number is less than 2000) is as follows:

$$P = 0.000273 Q l u / d^4$$

where,

P=pounds per square inch gauge

Q=gallons per minute

L=feet u=absolute viscosity in centipoise $d^4$=inside diameter of pipe in inches to the 4th power.

For an example (not shown), 20 feet of ⅜" 20 gauge tubing (0.305"id) flowing 0.25 gpm of 40 cps material has an individual pressure loss of 6.31 psi. As the viscosity is continuously monitored either manually or automatically, a thinner such as a solvent will be selectively added to the paint to thin the paint if the viscosity is too high. The solvents are typically added to the batch tank 22.

The paint system 10 is comprised of many different segments of tubing and hose, each having their own pressure loss due to variations in diameter and length. Accumulating all this data into one equation and solving for viscosity yields the following equations:

$$P = Cqu \text{ or } u = P/CQ$$

where, u=viscosity (40 cps typical)

C=a constant found by combining all the equations (0.10 for the example of FIG. 1)

P=the difference between the supply and return pressure (80 psi for the example of FIG. 1)

Q=gpm (20 gpm for the example of FIG. 1)

The present inventive viscosity regulation system for paint utilized in an automotive vehicle body paint application system has been shown in a preferred embodiment. However, it will be apparent to those skilled in the art that various modifications can be made to the present invention from that as described in the present specification and drawing without departing from the spirit and scope of the present invention as it is encompassed by the disclosure of the specification and drawings and by the following claims.

We claim:

1. A method of regulating the viscosity of a liquid paint in an automotive vehicle paint application system comprising:

pumping the paint into the paint application system at a first pressure;

continuously monitoring the first pressure that the paint is pumped into the paint application system;

returning the paint which is not applied to a vehicle body by the paint application system through a return line;

continuously monitoring the return pressure of the liquid paint flowing through the return line;

continuously measuring the flow rate of the liquid paint returning through the return line;

calculating the viscosity from the pressure differential from the first pressure and the return pressure and the fluid flow rate of the paint in the return line of the paint application system and a constant representative of the fluid resistance of the paint application system;

delivering the paint to a pressure sump from said return line; and selectively adding thinners to the liquid paint to cause the paint to maintain a predetermined level of viscosity.

2. A method of regulating the viscosity of a liquid paint in an automotive vehicle paint application system as described in claim 1, further including regulating the pressure of the return line.

3. A method of regulating the viscosity of a liquid paint in an automotive vehicle paint application system as described in claim 1, wherein an analog-type pressure transducer is utilized to determine the pressure on the paint delivered by the pump.

4. A method of regulating the viscosity of a liquid paint in an automotive vehicle paint application system as described in claim 1, wherein an analog-type pressure transducer continuously monitors the pressure in the return line.

5. A method of regulating the viscosity of a liquid paint in an automotive vehicle paint application system as described in claim 1, wherein solvent is added to the paint to thin the paint.

* * * * *